United States Patent [19]

Brouwer et al.

[11] 4,120,861

[45] Oct. 17, 1978

[54] 2-(5-PHENYL-1,3,4-THIADIAZOL-2-YL)BENZOIC ACID

[75] Inventors: Walter G. Brouwer, Guelph; Edwin J. MacPherson, Elmira, both of Canada; Ronald B. Ames, Naugatuck, Conn.; Robert W. Neidermyer, Cheshire, Conn.; Charles E. Crittendon, Cheshire, Conn.

[73] Assignees: Uniroyal, Inc., New York, N.Y.; Uniroyal Ltd., Ontario, Canada

[21] Appl. No.: 793,111

[22] Filed: May 2, 1977

Related U.S. Application Data

[62] Division of Ser. No. 648,237, Jan. 12, 1976, Pat. No. 4,035,175, which is a division of Ser. No. 492,376, Jul. 29, 1974, Pat. No. 3,947,263.

[51] Int. Cl.$^2$ .................................. C07D 285/12
[52] U.S. Cl. .................................. 260/302 D; 260/299
[58] Field of Search .................................. 260/302 D

[56] References Cited

U.S. PATENT DOCUMENTS 4,020,080  4/1977  Irick et al. .................... 260/302 D

FOREIGN PATENT DOCUMENTS 1,249,873  9/1967  Fed. Rep. of Germany ...... 260/302 D Primary Examiner—Alton D. Rollins
Attorney, Agent, or Firm—James J. Long

[57] ABSTRACT

Plant growth regulant effects, such as dwarfing, cessation of terminal growth, increased flower set, increased fruit and pod set, fruiting body abortion, twisting and epinastic responses, etc., may be accomplished on crops such as soybeans, cotton, etc., by application of certain 2-(1,3,4-oxadiazol-2-yl) or 2-(2-oxazolyl) or 2-(1,3,4-thiadiazol-2-yl)benzoic acids, salts and esters, having the formula

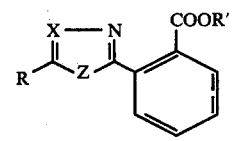

where X is nitrogen or C-R" (R" being hydrogen or methyl), Z is oxygen or sulfur when X is nitrogen, Z is oxygen when X is C-R", R is phenyl or various substituents, and R' is hydrogen or various substituents. An example is 2-(5-phenyl-1,3,4-oxadiazol-2-yl) benzoic acid. The compounds where X is nitrogen and Z is sulfur are new compounds, e.g., 2-(5-phenyl-1,3,4-thiadiazol-2-yl)benzoic acid.

1 Claim, No Drawings

2-(5-PHENYL-1,3,4-THIADIAZOL-2-YL)BENZOIC ACID

This is a division of our copending application Ser. No. 648,237, filed Jan. 12, 1976 (now U.S. Pat. No. 4,035,175, July 12, 1977) which is in turn a division of Ser. No. 492,376 filed July 29, 1974 (now U.S. Pat. No. 3,947,263, Mar. 30, 1976).

This invention relates to a method of regulating plant growth and to plant growth regulant compositions as well as to new 2-(1,3,4-thiadiazol-2-yl)benzoic acids, salts and esters.

Copending application Ser. No. 170,263, of Brouwer, MacPherson, Ames and Neidermyer, filed Aug. 9, 1971, now U.S. Pat. No. 3,882,138 issued May 6, 1975, discloses herbicidal action of certain 2-(1,3,4-oxadiazol-2-yl) and 2-(2-oxazolyl)benzoic acids, salts and esters. The present invention is directed to the use of said compounds, as well as certain new 2-(1,3,4-thiadiazol-2-yl)benzoic acids, salts and esters, as plant growth regulants.

The compounds employed in the present invention as plant growth regulants are benzoic acids (or salts or esters thereof) of the formula

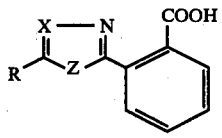

wherein:

X is nitrogen or C-R" (R" being hydrogen or methyl);

Z is oxygen or sulfur when X is nitrogen, Z is oxygen when X is C-R";

R is a heterocyclic group or the group

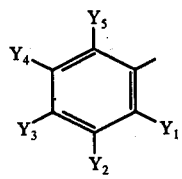

and the Y's are the same or different and are selected from the group consisting of hydrogen, halogen, nitro, lower alkyl, and lower alkoxy.

The compounds in which Z is sulfur, that is, the 2-(1,3,4-thiadiazol-2-yl)benzoic acids, salts and esters, are new chemicals.

One preferred sub-class of chemicals employed as plant growth regulants in the invention is that represented by the benzoic acids (or salts or esters thereof) of formula

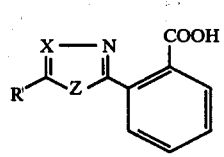

where X and Z have the values previously stated and R is phenyl, lower alkylphenyl (e.g., o-methylphenyl), lower alkoxyphenyl (e.g., 2-methoxyphenyl), halophenyl, nitrophenyl, heterocyclic (e.g., pyridyl, furyl) or substituted heterocyclic (e.g., trimethylfuryl).

In more detail, plant growth regulant compounds employed in the invention may be represented by the formula

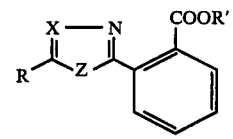

where X, Z and R are as previously defined and R' is hydrogen or a salt-forming or ester-forming moiety. When R' is hydrogen this formula of course represents the benzoic acids themselves. In the salts R' is typically an alkali metal (preferably sodium or potassium although lithium or other metal may also be used as the salt-forming moiety including polyvalent metals such as copper, zinc, calcium, barium, magnesium, iron [ferric or ferrous] aluminum, and the like), ammonium, alkylammonium having up to 12 carbon atoms (e.g., methylammonium, ethylammonium, diethylammonium, hexylammonium, dodecylammonium), alkanolammonium having up to 12 carbon atoms (e.g., ethanolammonium, diethanolammonium, hexanolammonium, dodecanolammonium), choline, and the like. In the esters, R' is commonly represented by aliphatic or cycloaliphatic hydrocarbyl moieties having up to 12 carbon atoms, notably alkyl (e.g., methyl, ethyl, n-propyl, isopropyl, n-butyl, iso-butyl, sec.-butyl, tert.-butyl, etc.), alkenyl (e.g., allyl, methallyl, etc.), alkynyl (e.g., 2-propynyl, 2-butynyl, etc.), and the like, or by epoxyalkyl (e.g., 2,3-epoxypropyl, 2,3-epoxybutyl, 3,4-epoxybutyl, etc.). In addition to the acids themselves (R' is hydrogen) preferred bodies are the alkali metal salts (R' is alkali metal) and the alkyl esters (R' is alkyl).

Also particularly advantageous in certain respects are chemicals in which the 5-substituent (R) on the oxazole, oxadiazole or thiadiazole ring is phenyl, that is, $Y_1$, $Y_2$, $Y_3$, $Y_4$ and $Y_5$ are all hydrogen, or a mono-substituted phenyl, that is, all but one of $Y_1$, $Y_2$, $Y_3$, $Y_4$ and $Y_5$ are hydrogen (although di-, tri-, tetra- and penta-substituted phenyl as defined herein may also be used).

Examples of oxadiazoles, oxazoles and thiadiazoles useful in plant growth regulation in accordance with the invention are 2-(5-phenyl-1,3,4-oxadiazol-2-yl)benzoic acid, the methyl ester of same, the ethyl ester of same, the butyl ester of same, (or similar alkyl esters in which the alkyl group is normal or iso, primary, secondary, or tertiary, straight chain or branched), 2-[5-(2-tolyl)-1,3,4-oxadiazol-2-yl]benzoic acid (also the m-methylphenyl and p-methylphenyl analogs of same), ethyl 2-[5-(2,3-dimethylphenyl)-1,3,4-oxadiazol-2-yl]benzoate, amyl 2-[5-(2,3,4-trimethylphenyl)-1,3,4-oxadiazol-2-yl]benzoate, 2-[5-(4-chlorophenyl)-1,3,4-oxadiazol-2-yl]benzoic acid, methyl 2-[5-(2,3,4-tribromophenyl)-1,3,4-oxadiazol-2-yl]benzoate, 2-[5-(3-nitrophenyl)-1,3,4-oxadiazol-2-yl]benzoic acid, isopropyl 2-[5-(2-chloro-3-nitro-4-methoxyphenyl)-1,3,4-oxadiazol-2-yl]benzoate, methyl 2-[5-(2,3,4-trimethoxyphenyl)-1,3,-oxadiazol-2-yl]benzoate, butyl 2-(5-phenyl-2-oxazolyl)benzoate, 2-[5-(2-nitrophenyl)-2-oxazolyl]benzoic acid, 2-[5-(2,3,4-trichlorophenyl)-2-oxazolyl]benzoic acid, sodium 2-[5-(2,3,4-trichlorophenyl)-2-oxazolyl]benzoate, ethyl 2-[5-(2,3,4,5-tetrachlorophenyl)-1,3,4-oxadiazol-2-yl]benzoate, ethyl 2-[5-

(2,3,4,5,6-pentachlorophenyl)-1,3,4-oxadiazol-2-yl]benzoate, potassium 2-(5-phenyl-2-oxazolyl) benzoate, ammonium 2-[5-phenyl-1,3,4-oxadiazol-2-yl]benzoate, 2-[5-(5-chloro-3-pyridyl)-1,3,4-oxadiazol-2-yl]benzoic acid n-butyl 2-(5-phenyl-2-oxazolyl) benzoate, allyl 2-[5-(4-nitrophenyl)-1,3,4-oxadiazol-2-yl]benzoate, methallyl 2-(4-methyl-5-phenyl-2-oxazolyl) benzoate, propyl 2-[5-(2-chlorophenyl)-1,3,4-oxadiazol-2-yl]benzoate, butyl 2-(4-methyl-5-phenyl-2-oxazolyl)benzoate, 2,3-epoxypropyl2-(5-phenyl-1,3,4-oxadiazol-2-yl)benzoate, ferric tri[2-(5-phenyl-1,3,4-oxadiazol-2-yl)benzoate], manganese di[2-(5-phenyl-2-oxazolyl)benzoate], 2-[5-(3,4,5-trimethoxyphenyl)-1,3,4-oxadiazol-2-yl]benzoic acid, n-butyl 2-(1,3,4-oxadiazol-2-yl)benzoate, 2-[5-(2,4,5-trimethyl-3-furyl)-1,3,4-oxadiazol-2-yl]benzoic acid, 2-[5-(2-furyl)-1,3,4-oxadiazol-2-yl]benzoic acid, 2-[5-(2,5-dimethyl-3-furyl)-1,3,4-oxadiazol-2-yl]benzoic acid, 2-[5-(2-methyl-3-furyl)-1,3,4-oxadiazol-2-yl]benzoic acid, 2-[5-(3-furyl)-1,3,4-oxadiazol-2-yl]benzoic acid, 2-[5-(3-pyridyl)-1,3,4-oxadiazol-2-yl]benzoic acid, and the like.

Preferred plant growth regulating chemicals employed in the invention are those selected from the group consisting of 2-(5-phenyl-1,3,4-oxadiazol-2-yl)benzoic acid, 2-[5-(2-tolyl)-1,3,4-oxadiazol-2-yl]benzoic acid, 2-[5-(4-chlorophenyl)-1,3,4-oxadiazol-2-yl]benzoic acid, 2-[5-(2-chlorophenyl)-1,3,4-oxadiazol-2-yl]benzoic acid, 2-[5-(3-chlorophenyl)-1,3,4-oxadiazol-2-yl]benzoic acid, 2-[5-(3-pyridyl)-1,3,4-oxadiazol-2-yl]benzoic acid, 2-(5-phenyl-2-oxazolyl)benzoic acid, 2-[5-(2-methoxyphenyl)-1,3,4-oxadiazol-2-yl]benzoic acid, propargyl 2-(5-phenyl-1,3,4-oxadiazol-2-yl)benzoate, 2-(4-methyl-5-phenyl-2-oxazolyl)benzoic acid, butyl 2-(5-phenyl-1,3,4-oxadiazol-2-yl)benzoate, 2-[5-(3-nitrophenyl)-1,3,4-oxadiazol-2-yl]benzoic acid, 2-[5-(2,4,5-trimethyl-2-furyl)-1,3,4-oxadiazol-2-yl]benzoic acid, methyl 2-(5-phenyl-1,3,4-oxadiazol-2-yl)benzoate, methyl 2-(5-phenyl-2-oxazolyl)benzoate, and 2-(5-phenyl-1,3,4-thiadiazol-2-yl)benzoic acid.

The 2-(1,3,4-oxadiazol-2-yl)benzoic acid plant growth regulant chemicals employed in the invention may be prepared as disclosed in application Serial No. 170,263 referred to above, the disclosure of which is hereby incorporated herein by reference.

The new 2-(1,3,4-thiadiazol-2-yl)benzoic acid plant growth regulant chemicals of the invention may be prepared by the aqueous permanganate oxidation of 2-methylphenyl-5-phenyl-1,3,4-thiadiazoles.

In accordance with the invention, a 2-(1,3,4-oxadiazol-2-yl) or 2-(2-oxazolyl) or 2-(1,3,4-thiadiazol-2-yl)benzoic acid chemical of the kind described is applied to plants in an amount effective to regulate the growth of the plants. Regulation of the growth of plants is frequently desirable for a number of reasons. Thus, useful plant growth regulant effects contemplated by the invention include:
 a. Dwarfing;
 b. Cessation of terminal growth
 c. Increased flower set;
 d. Fruit and pod set;
 e. Fruiting body abortion; and
 f. Twisting and epinastic responses.

Other useful effects include forced axillary growth when the chemical is applied to retard vegetative growth. Also, the flowering characteristics of certain species can be altered such as in monocots to facilitate sterility. In sugar-producing species (e.g., sugar cane, sugar beets), a positive increase in percent sugar can be obtained.

Control of lodging is an important plant growth regulant effect of the present chemicals. For example when soybeans are harvested, many bushels of plants per acre are frequently lost due to lodged plants. A common soybean combine is not capable of harvesting lodged plants. By application of the present chemicals, dwarfing may be accomplished and lodging prevented.

In all cotton producing areas there are times when climatic conditions increase the vegetative growth of the cotton; the result is called "rank cotton". The chemicals described herein stop this rank growth by preventing terminal vegetative growth, thus forcing the plant to continue its reproductive activity.

In areas where a second crop of cotton is planted and harvested the same year, many times the cotton matures too late. This slows down the planting of subsequent crops and in some cases may completely eliminate the planting of that crop. The chemicals herein described, when applied to cotton that is in the 80% boll set stage, will abort any subsequent flowers. This hastens the maturity of the existing cotton bolls and hence allows early harvesting. This phenomenon may also be called a "cut off spray".

Further plants on which the present growth regulant chemicals are useful include peanuts and small grains, such as rye and the various cereal grain type plants, e.g., wheat, barley, oats, and the like.

While it is not desired to limit the invention to any particular theory of operation, it can be postulated from the results obtained with the present plant growth regulating chemicals that the chemicals effect a basic metabolic change in the plant that increases the sugar level directly or prevents the breakdown of sugars.

In one aspect, the invention is directed to plant growth retardation. Various plant growth regulant effects noted above are directly or indirectly related to retardation in many cases, that is, certain desirable effects including control of lodging, prevention of terminal vegetative growth, and other effects, may be regarded as manifestations of, or side effects of retardation in one form or another. Thus, when the chemical is applied to retard vegetative growth, forced axial growth may occur; application of the chemical to accomplish dwarfing may prevent lodging; etc. The effects with which the invention is concerned are of course non-herbicidal effects, that is, the present chemicals are employed in amount insufficient to injure the plants to which they are applied.

To use the present chemicals as plant growth regulants, the chemical is applied to a locus where such control is to be effected in an amount sufficient to regulate the growth of the plant in the manner desired. The amount employed follows conventional practice for plant growth regulants, and is frequently in the range of from 0.02 to 10 pounds per acre, depending on the plant species being treated. The chemical is suitably applied as a formulation in accordance with conventional agricultural chemical practice.

Thus, the chemical may be impregnated on finely-divided or granular inorganic or organic carriers such as attapulgite clay, sand, vermiculite, corn cobs, activated carbon or other granular carriers known to the art. The impregnated granules may then be spread on the soil. Furthermore, the chemical may be formulated, for example, as a wettable powder by impregnating an inactive powdered carrier to which a surface active dispersing agent has been added. Typical powdered solid carriers are the various mineral silicates, e.g., mica, talc, pyrophyllite and clays. The wettable powder may then be dispersed in water and sprayed on plants, or the soil surface, or plants to be prepared for harvesting. Similarly, an emulsifiable concentrate may be prepared by dissolving the chemical in a suitable solvent to which a surface active dispersing agent has been added. The emulsifiable concentrate may then be dispersed in water and applied by spraying. A soluble concentrate may be prepared by reacting the chemical with a stoichiometric quantity of base to which a surface active wetting agent has been added. This formulation may also be applied to foliage by spraying. Suitable surface active agents are well known to those skilled in the art and reference may be had to McCutcheon's Detergents and Emulsifiers, 1970, Allured Publishing Corp., Ridgewood, N.J., or Hoffman et al., U.S. Pat. Nos. 2,614,916, cols. 2 to 4 and 2,547,724, cols. 3 and 4, for examples of appropriate surface active agents.

The concentration of active chemical in the formulation may vary widely, e.g. from 10 to 95%. The concentration of active chemical in a dilution applied to the soil or foliage is almost invariably from 0.001% to 75%. Some of these chemicals are active at very low dosages and therefore the plant growth regulation properties should not be confused with the herbicidal properties which were found when the chemical was applied at higher rates.

The following Examples will serve to illustrate the practice of the invention in more detail.

EXAMPLE 1

2-(5-Phenyl-1,3,4-thiadiazol-2-yl)benzoic acid was prepared by the following method.

2-o-Methylphenyl-5-phenyl-1,3,4-thiadiazole (25 g.) was suspended in a solution of potassium permanganate (40 g.) in water (475 ml.). The reaction mixture was stirred and refluxed until the color of permanganate had discharged, then filtered and cooled. Unreacted 2-o-methylphenyl-5-phenyl-1,3,4-thiadiazole which separated was removed by filtration. When this filtrate was acidified, 2-(5-phenyl-1,3,4-thiadiazol-2-yl)benzoic acid was obtained and recrystallized from ethanol to give white crystals, M.P. 178°–180°. Analysis gave C, 63.37; H, 3.74; N, 9.74. $C_{15}H_{10}N_2O_2S$ requires C, 63.83; H, 3.51; N, 9.93.

EXAMPLE 2

This Example illustrates the growth regulating properties of the chemicals on four crops; Pinto Beans — *Phaseolus vulgaris*; Cotton — *Gossypium hirsutum*; Peanuts — *Arachis hypogaea* and Oats — *Avena sativa*. Six hundred mg of chemical are dissolved in 10 ml acetone and 30 mg of Triton X100 (trademark; isooctyl phenyl poly ethoxy ethanol). This mixture was diluted to a 100 ml volume with distilled water.

Respective concentrations of 2000 and 1000 ppm are made from the 6000 ppm stock. The appropriate mixture was sprayed to runoff on the four species aforementioned. The plants were sprayed with a DeVilbiss atomizing sprayer at the following stages of growth
Pinto Beans — very early 1st trifoliate
Cotton — Fully expanded primary leaf stage
Peanuts — 2–4 leaf stage
Oats — 2–4 leaf stage
Subjective plant growth regulant observations were made from five days after spraying through three weeks. These observations included retardation, formative effects and phytotoxicity. These data are presented in TABLE I, wherein the chemicals employed are identified by the letters A through P as follows:

A. 2-(5-Phenyl-1,3,4-oxadiazol-2-yl)benzoic acid.
B. 2-[5-(2-Tolyl)-1,3,4-oxadiazol-2-yl]benzoic acid.
C. 2-[5-(4-Chlorophenyl)-1,3,4-oxadiazol 2-yl]benzoic acid.
D. 2-[5-(2-Chlorophenyl)-1,3,4-oxadiazol-2-yl]benzoic acid.
E. 2-[5-(3-Chlorophenyl)-1,3,4-oxadiazol-2-yl]benzoic acid.
F. 2-[5-(3-Pyridyl)-1,3,4-oxadiazol-2-yl]benzoic acid.
G. 2-(5-Phenyl-2-oxazolyl)benzoic acid.
H. 2-[5-(2-Methoxyphenyl)-1,3,4-oxadiazol-2-yl]benzoic acid.
I. Propargyl 2-(5-phenyl-2-oxadiazol-2-yl)benzoate.
J. 2-(4-Methyl-5-phenyl-2-oxazolyl)benzoic acid.
K. Butyl 2-(5-phenyl-1,3,4-oxadiazol-2-yl) benzoate.
L. 2-[5-(3-Nitrophenyl)-1,3,4-oxadiazol-2-yl]benzoic acid.
M. 2-[5-(2,4,5-Trimethyl-2-furyl)-1,3,4-oxadiazol-2-yl]benzoic acid.
N. Methyl 2-(5-phenyl-1,3,4-oxadiazol-2-yl) benzoate.
O. Methyl 2-(5-phenyl-2-oxazolyl)benzoate.
P. 2-(5-Phenyl-1,3,4-thiadiazol-2-yl)benzoic acid.

TABLE I

| | Plant Growth Regulation | | |
|---|---|---|---|
| Chemical | Rate PPM | Crop | Plant Growth Regulating Response |
| A | 2000 | Pinto Bean | Severe epinasty and retarding and twisting |
| B | 2000 | Pinto Bean | Severe retardation and trifoliates inhibited |
| B | 6000 | Peanuts | 80% retarded and severe epinasty |
| C | 2000 | Pinto Bean | Trifoliates inhibited + severe epinasty |
| C | 6000 | Cotton | 80% retarded |
| | | Peanuts | 80% retarded |
| D | 2000 | Pinto Bean | 80–100% retardation; moderate epinasty |
| D | 6000 | Peanuts | Moderate epinasty |
| E | 1000 | Pinto Bean | Moderate epinasty, 80–100% retardation |
| | | Cotton | Severe epinasty |
| | | Peanut | 50–60% retardation; moderate epinasty |
| F | 2000 | Pinto Bean | 80–100% retardation; terminals killed |
| F | 6000 | Cotton | Moderate epinasty |
| | | Peanut | Moderate epinasty |
| G | 1000 | Pinto Bean | 80% retardation; terminals inhibited |
| G | 6000 | Cotton | 20% retardation |
| G | 6000 | Peanut | 60% retardation |
| G | 6000 | Oat | 20% retardation |
| H | 1000 | Pinto Bean | 80% retardation |
| H | 6000 | Peanut | 20% retardation |
| H | 6000 | Oat | 20% retardation |
| I | 1000 | Pinto Bean | Severe epinasty 100% retardation |
| | | Cotton | 20% retardation |
| | | Peanuts | 20% retardation |
| | | Oats | 20% retardation |
| J | 6000 | Cotton | New Growth twisted + 30% retarded |
| | | Peanut | 50% retarded |
| | | Oat | 80% retarded |
| K | 6000 | Cotton | Trifoliates 80% retarded & deformed |
| | | Peanut | Slight twisting; 30% retarded |
| | | Oat | 80% retarded |
| L | 6000 | Cotton | Leaves stunted |
| | | Peanut | Moderately retarded |
| M | 1000 | Pinto Bean | Trifoliates retarded, forced axillary growth |
| | 6000 | Peanuts | Twisted |
| N | 1000 | Tomato | Severely epinasty |
| | | Pinto Bean | 100% retarded |
| | 6000 | Cotton | 30% retarded |

TABLE I-continued

| Chemical | Rate PPM | Plant Growth Regulation Crop | Plant Growth Regulating Response |
|---|---|---|---|
| O | 1000 | Pinto Bean | 80% retarded |
| O | 6000 | Peanut | Moderate epinasty |
| P | 2000 | Pinto Bean | 100% retarded, terminals killed |
| P | 6000 | Peanut | 50% retardation |

EXAMPLE 3

This Example illustrates the growth retarding effects of the present chemicals on soybeans, *Glycine max*. Twelve mg of chemical are dissolved in 10 ml acetone and 30 mg Triton X100 (isooctyl phenyl poly ethoxyethanol). This mixture was diluted to a 100 ml volume with distilled water, making it a 120 ppm solution. Respective concentrations of 60 and 30 ppm are made from the 120 ppm stock solution. Three pots containing two soybean plants at the fully expanded first trifoliate leaf stage are sprayed to run-off with a DeVilbiss atomizing sprayer. The plants are placed in the greenhouse. The plants are measured at spraying time and when the control plants begin to pod or approximately four weeks after spraying. The actual measurement used for evaluation is the difference in growth from first measurement to the last measurement. A percent growth figure is obtained by using the following formula:

$$\frac{\text{Growth of control in cm} - \text{Growth of treated in Cm}}{\text{Growth of Control in cm}} \times 100 = \% \text{ retardation}$$

The results are shown in TABLE II, wherein the letters represent various chemicals identified in Example 2.

TABLE II

| Chemical | Rate PPM | Retardation of Soybeans % Retardation |
|---|---|---|
| A | 30 | 78 |
| A | 60 | 83 |
| B | 30 | 42 |
| B | 60 | 69 |
| B | 120 | 75 |
| C | 30 | 89 |
| C | 60 | 88 |
| C | 120 | 94 |
| D | 30 | 80 |
| D | 60 | 86 |
| D | 120 | 91 |
| F | 30 | 57 |
| F | 60 | 73 |
| F | 120 | 80 |
| H | 30 | 43 |
| H | 60 | 68 |
| H | 120 | 78 |
| G | 30 | 83 |
| G | 60 | 89 |
| I | 30 | 66 |
| I | 60 | 74 |
| I | 120 | 82 |
| J | 30 | 45 |
| J | 60 | 57 |
| J | 120 | 70 |
| K | 30 | 50 |
| K | 60 | 58 |
| K | 120 | 75 |

EXAMPLE 4

This Example further illustrates practice of the invention on cotton.

One hundred mg of chemical formulated in a three pound active gallon (see Example 6-i for composition) were dissolved in 400 ml of water. This solution has a concentration of 1000 ppm. Respective concentrations of 500 and 250 ppm were made by diluting the stock solution of 1000 ppm. Four cotton seeds, *Gossypium hirsutum*, variety Stoneville 213, were planted in six-inch pots. The pots were eventually thinned to one plant per pot. The spray application was made when the plants had developed two bolls one inch in diameter. Three plants were used for each chemical treatment which was applied to run-off with a DeVilbiss atomizing sprayer. The last terminal boll that was one-half inch in diameter was marked with a "twistem". The cotton was allowed to mature seven weeks beyond spray application before data were taken. The data consisted of measuring the growth in cm from the marked boll to the terminal growing point and also the number of bolls that developed beyond the marked boll were counted. The percent decrease in height and number of bolls was calculated by using the following formula.

$$\frac{\text{Height in cm of check} - \text{Height in cm of treated}}{\text{Height in cm of Check}} \times 100 = \% \text{ retardation}$$

The data are given in Table II, illustrating the dramatic reduction in height and boll number due to the chemical application.

TABLE II

| Chemical | Growth Regulation on Cotton Rate PPM | % Retardation | % Decrease in Boll Number |
|---|---|---|---|
| A | 250 | 49 | 51 |
| A | 500 | 40 | 57 |
| A | 1000 | 42 | 64 |
| G | 250 | 19 | 51 |
| G | 500 | 23 | 51 |
| G | 1000 | 37 | 51 |

EXAMPLE 5

To illustrate further the growth regulating properties of the chemicals on the metabolic activity of plants, 10.5 ml of formulation (formulated as a three pound active gallon — see Example 6-ii for composition) were diluted to a 1892 ml volume with water. This solution was equivalent to 0.5 lb. active chemical in 30 gal. water per acre when applied to sugarbeets, *Beta vulgaris*, six weeks before harvest.

The yield data were determined by hand harvesting each of three treatment replicates which consisted of one row fifteen feet long. The sugar content was determined by measuring the sucrose content of beets that were randomly selected from each plot.

The data are given in TABLE IV, illustrating the increase in sugar content due to the chemical application.

TABLE IV

| Chemical | Increase in Sugar Rate Lbs./Acre | % Sugar |
|---|---|---|
| A | ¼ | 15.48 |
| A | ½ | 15.76 |
| A | 1 | 15.18 |
| Control |  | 14.85 |

Based on an average yield of 40,000 pounds of beets per acre, the 0.91% increase over the control would bring the farmer 364 extra pounds of sugar per acre.

EXAMPLE 6

Listed below are non-limiting examples of formulations which can be prepared with chemicals of this invention.

| | g |
|---|---|
| i. 36% active by volume (3 lb/gallon soluble liquid) | |
| a. 2-(5-Phenyl-1,3,4-oxadiazol-2-yl)benzoic acid | 36.0 |
| b. NH$_4$OH (58.6%) | 17.0 |
| c. Water | 57.0 |
| ii. 30% active by volume (3 lb/gallon soluble liquid) | |
| a. 2-(5-Phenyl-1,3,4-oxadiazol-2-yl)benzoic acid | 36.0 |
| b. NH$_4$OH (58.6%) | 22.0 |
| c. Dowfac (trademark) 2A1 (solution) sodium dodecyldiphenyl ether disulfonate | 2.25 |
| d. Water | 59.75 |
| iii. 22% active by volume (2 lb/gallon soluble liquid) | |
| a. 2-(5-Phenyl-1,3,4-oxadiazol-2-yl)benzoic acid | 24.0 |
| b. KOH (95.5%) | 6.0 |
| c. Water | 78.8 |
| iv. 10% active granule | |
| a. 2-(5-Phenyl-1,3,4-oxadiazol-2-yl)benzoic acid | 30.0 |
| b. NH$_4$OH (58.6%) | 13.2 |
| c. Water | 31.8 |
| d. 25/50 mesh RVM Attaclay (trademark) attapulgite clay | 270.0 |

We claim:
1. 2-(5-Phenyl-1,3,4-thiadiazol-2-yl)benzoic acid.

* * * * *